United States Patent
Turchetta et al.

(10) Patent No.: US 6,897,339 B2
(45) Date of Patent: May 24, 2005

(54) PROCESS FOR THE PRODUCTION OF HIGH PURITY IOHEXOL

(75) Inventors: Stefano Turchetta, Rome (IT); Pietro Massardo, Rome (IT); Valentina Aromatario, Rome (IT)

(73) Assignee: Chemi, S.p.A., Milan (IT)

( * ) Notice: Subject to any disclaimer, the term of this patent is extended or adjusted under 35 U.S.C. 154(b) by 0 days.

(21) Appl. No.: 10/474,535

(22) PCT Filed: Apr. 9, 2002

(86) PCT No.: PCT/IB02/01256

§ 371 (c)(1),
(2), (4) Date: Oct. 10, 2003

(87) PCT Pub. No.: WO02/083623

PCT Pub. Date: Oct. 24, 2002

(65) Prior Publication Data

US 2004/0106828 A1 Jun. 3, 2004

(30) Foreign Application Priority Data

Apr. 11, 2001 (IT) .................................. MI2001A0773

(51) Int. Cl.⁷ ..................... C07C 233/05; C07C 233/64
(52) U.S. Cl. ..................................... 564/153; 424/9.452
(58) Field of Search ........................ 564/153; 424/9.452

(56) References Cited

U.S. PATENT DOCUMENTS

| 4,250,113 A | 2/1981 | Nordal et al. |
| 5,204,086 A | 4/1993 | Wille |

FOREIGN PATENT DOCUMENTS

| EP | WO 98 08804 A | 3/1998 |
| EP | 0 919 540 A | 6/1999 |

*Primary Examiner*—Shailendra Kumar
(74) *Attorney, Agent, or Firm*—Clark & Elbing, LLP

(57) ABSTRACT

Purification process of iohexol comprising the treatment of said product with 1-methoxy-2-propanol either alone or mixed with other solvents.

11 Claims, No Drawings

PROCESS FOR THE PRODUCTION OF HIGH PURITY IOHEXOL

CROSS-REFERENCE TO RELATED APPLICATION

This application claims priority from International Patent Application PCT/IB02/01256 entitled "Process for the Production of High Purity iohexol," filed Apr. 9, 2002, which claims priority from italian Patent Application MI2001A000773 entitled "Process for the Production of High Purity iohexol," filed on Apr. 11, 2001, the contents of which are incorporated by reference herein in their entirety.

FIELD OF THE INVENTION

The present invention relates to a purification process of iohexol.

BACKGROUND ART

Iohexol belongs to the class of non-ionic contrast media. Together with iopamidol, it is one of the most used products in diagnostic x-ray procedures, since it presents a number of advantages over other contrast media, mainly in terms of tolerability.

Since X-ray inspections usually require a large amount of product (up to 200 g per patient), it derives that purity is fundamental for biomedical use.

The last step of the chemical synthesis of iohexol, as disclosed in U.S. Pat. No. 4,250,113 and subsequent patent-literature, is an alkylation reaction in a basic environment on an amide with an alkyl halide di-hydroxylated:

(SCHEME 1)

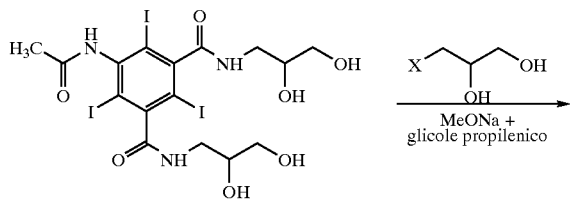

This inevitably leads to the development of O-alkylated by-products (O-alkylates),

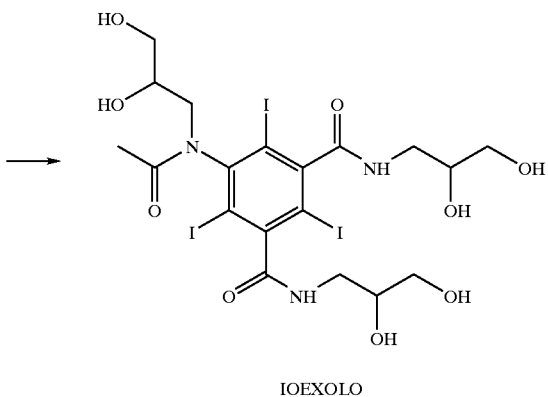

IOEXOLO which are very difficult to eliminate due their resemblance to iohexol. Numerous methods of iohexol purification are described in literature. U.S. Pat. No. 4,250,113 discloses the use of butanol as the final crystallization solvent, but said technique is not completely effective in eliminating the O-alkylates.

EP919540 discloses that ethanol crystallization can reduce the content in O-alkylate substances. Nevertheless, the examples provided show that, in the best case, the 1.3% initial content in O-alkylates is reduced to 0.55%. The purification value thus obtained is just slightly lower than the limit fixed by European Pharmacopea (0.6%).

U.S. Pat. No. 5,204,086 discloses that the crystallization with i-PrOH is effective in eliminating the O-alkylate impurities from iohexol only by 25÷30%.

In WO9808804, methoxy-ethanol and mixtures thereof with isopropanol are used both in iohexol crystallization and in the last step. Nevertheless, the examples provided show that said technique is scarcely effective in eliminating the O-alkylate substances, the 0.68% initial value thereof being reduced to 0.51%.

Further, the methoxy-ethanol can cause damages to the reproductive system, sterility and foetal malformations.

As a matter of fact, there is still a great need for an easy, sure and effective method for the elimination of iohexol impurities, particularly O-alkylates.

SUMMARY

During studies designed to meet this requirement, it has been unexpectedly found that the 1-methoxy-2-propanol, either alone or optionally mixed with other solvents, is very effective in eliminating the impurities, particularly O-alkylates, from raw iohexol either by means of pulping treatments and further filtration of the suspension obtained or by solution crystallization.

DETAILED DESCRIPTION OF THE INVENTION

Particularly, the process disclosed in the present invention comprises the following steps:
a) adding iohexol to a quantity of 1-methoxy-2-propanol comprised between 0.5 and 1000 volumes;
b) heating the mixture to reflux. When a solvent ratio is used which ranges between 1:1 and 1:50 w/v, a suspension is obtained; otherwise, if higher quantities of solvent are used in the given range, a solution is obtained;
c) cooling the mixture at room temperature;
d) filtering the solid, whether obtained from the suspension or by solution crystallization.

The purification process object of the present invention can also comprise a further final step (e) consisting in washing the solid obtained with 1-methoxy-2-propanol. Said washing phase further reduces the residual content of impurities.

In order to eliminate even the residual traces of solvent being still contained in the product, the latter is dissolved in water and the water is eliminated by evaporation, in such a way that the residual solvents are azeotropically removed. In this way, a residual solvent content can be achieved, which is lower than 100 ppm.

The purification process is repeatable.

As mentioned hereinabove, 1-methoxy-2-propanol according to the present invention can be also mixed with other solvents, said solvents being preferably isopropanol and water.

Particularly, when the process according to the present invention comprises a mixture of 1-methoxy-2-propanol and water, the phases (a) and (b) are carried out as follows:
a') suspending iohexol in 1-methoxy-2-propanol and adding water to facilitate the dissolution of the product;
b') removing water by azeotrope distillation with 1-methoxy-2-propanol; adding fresh 1-methoxy-2- propanol to replace the distilled one; heating the mixture thus obtained under reflux.

Alternatively, it is possible to start from a water solution containing 30–50% by weight of iohexol, to which 1-methoxy-2-propanol is subsequently added. In this case, the process according to the present invention is preferably carried out as follows:

a") adding a quantity ranging from 10 to 40 volumes of 1-methoxy-2-propanol to the water solution, depending on the quantity of iohexol;

b") distilling the solvent at atmospheric pressure until the temperature of the distillation heads being collected is within 115 to 120° C. and keeping the mixture thus obtained under reflux for approx 4 hours.

By the purification process according to the present invention, iohexol with a purity degree greater than 98% is obtained and the content of O-alkylate impurities is reduced by 55% to 95% of initial content.

In other words, the content of O-alkylate residues in the final product is 2 to 14 times lower than the initial content.

The present invention will be better understood by reference to the examples illustrated hereinafter, which are to be regarded as not limitative.

EXAMPLE 1

In a 2-l reactor, 1000 ml of methoxy-2-propanol is added to 200 g of raw iohexol with the following features: 91% HPLC purity, 2.2% O-alkylated Σ impurities and 0.1% water. The mixture was brought to reflux and held there for 4 h. After cooling to room temperature, the solid was next filtered from the solution and then washed with 2×100 ml of 1-methoxy-2-propanol.

After drying under vacuum at 50° C. for 12 h, 150 g of iohexol with >99% degree of purity was obtained. The content of O-alkylated impurities was 0.3%.

EXAMPLE 2

31 ml of 1-methoxy-2-propanol was added to 5 g of raw iohexol with 91% purity and 2.2% O-alkylate compounds. The mixture was brought to reflux and then 3 ml of water was added. 5 ml of solvent was then distilled and reintegrated with 5 ml of 1-methoxy-2-propanol. After 3 h reflux, the mixture was cooled to room temperature and the solid filtered and washed with 2×3 ml of solvent. After drying under vacuum at 50° C., 3.8 g of iohexol with 99% degree of purity was obtained. The content of O-alkylated impurities was 0.15%.

EXAMPLE 3

40 g of iohexol aqueous solution containing 15.6 g of product was placed into a 500 ml reactor. 290 ml of 1-methoxy-2-propanol was added to the solution, which was then heated and the solvent distilled until the temperature of the heads was 115÷120° C. The mixture was held in such conditions for 4 h, and then cooled at room temperature. The precipitate was filtered, washed with 20 ml of 1-methoxy-2-propanol and then discharged. 15.9 g of wet product=11.5 g of dried iohexol was obtained. 76% yield.

EXAMPLE 4

5 g of iohexol with 94% degree of purity and 2% O-alkylate compounds was suspended in 50 ml of 1-methoxy-2-propanol; the mixture was brought to reflux and held there for 5 h. This was then cooled to room temperature; the suspended solid was filtered and washed with 2×5 ml of 1-methoxy-2-propanol. 3.3 g of iohexol with 98.8% degree of purity and 0.4% O-alkylated impurities was obtained.

EXAMPLE 5

A 4 g sample of iohexol with 91% degree of purity and 3% O-alkylated impurities was suspended in 20 ml of 1-methoxy-2-propanol. The mixture was brought to reflux for 6 h, and then cooled up to room temperature. The solid was then filtered and washed with 2×3 ml of 1.methoxy-2-propanol. The wet solid was resuspended in 20 ml of 1-methoxy-2-propanol, brought to reflux and held there for additional 4 h. Then, the mixture was cooled at room temperature again and the suspended solid was filtered. After washing with 2×3 ml of 1-methoxy-2-propanol and drying under vacuum at 50° C. for 12 hours, 2.9 g of iohexol with 99% degree of purity and a content of 0.6% O-alkylated compounds was obtained.

EXAMPLE 6

6 g of iohexol with 94% degree of purity and 1.5% O-alkylated impurities was suspended in 30 ml of 1-methoxy-2-propanol to which 3 ml of isopropanol was added. The mixture was brought to reflux and held there for 6 h, and then cooled to room temperature. The resulting solid was filtered and washed with 2×5 ml of 1-methoxy-2-propanol. After drying under vacuum at 50° C. for 12 h, 4.2 g of iohexol with degree of purity >99% and 0.3% O-alkylated impurities was isolated.

What is claimed is:

1. A purification process of iohexol comprising:
    a) adding iohexol to a solvent comprising 1methoxy-2-propanol;
    b) heating the mixture to reflux;
    c) cooling the mixture to room temperature; and
    d) filtering the solid obtained.

2. The process according to claim 1, wherein steps (b) and (c) are carried out through hot pulping and remotion by filtration of the solution thus obtained.

3. The process according to claim 1, wherein steps (b) and (c) are carried out through hot dissolution and crystallization by cooling of the solution.

4. The process according to claim 1, wherein the 1-methoxy-2-propanol is used mixed with other solvents selected from the group consisting of water and/or isopropanol.

5. A purification process for preparing iohexol comprising the following steps:
    a) adding iohexol to a solvent comprising 1-methoxy-2-propanol in a quantity comprised between 0.5 and 1000 volumes;
    b) heating the mixture to reflux;
    c) cooling the mixture to room temperature; and
    d) filtering the solid obtained.

6. The process according to claim 5, wherein when the quantity of solvent is comprised between 1 and 50 volumes, and after heating to reflux, a suspension is obtained, which is cold-filtered.

7. The process according to claim 5, wherein when the quantity of solvent is comprised between 50 and 1000 volumes, and after heating to reflux, a solution is obtained, which, after cooling, gives a crystalline product that is next filtered.

8. The process according to claim 5, further comprising a step (e) consisting of washing the solid obtained with 1-methoxy-2-propanol.

9. The process according to claim 4, comprising the following steps, when water is used as co-solvent:
- a') suspending iohexol in 1-methoxy-2-propanol and adding water;
- b') distilling water from the reaction mixture, adding fresh 1-methoxy-2-propanol to replace that which was removed as azeotrope with water, and heating the mixture obtained under reflux;
- c) cooling the mixture to room temperature; and
- d) filtering the solid obtained.

10. The process according to claim 9, wherein the filtered product is dissolved in water, and the water and the water-azeotrope are eliminated by distillation up to reaching a residual solvent content lower than 100 ppm.

11. The process according to claim 4, comprising the following steps when water is used as co-solvent:
- a") adding a quantity of 1-methoxy-2-propanol between 10 and 40 volumes based on the quantity of iohexol, to an aqueous solution containing 30–50% by weight of iohexol;
- b") distilling the solvent at atmospheric pressure until the temperature of the distillation heads being collected is within 115 to 120° C. and keeping the mixture thus obtained under reflux for approximately 4 hours;
- c) cooling the mixture to room temperature; and
- d) filtering the solid obtained.

* * * * *

UNITED STATES PATENT AND TRADEMARK OFFICE
CERTIFICATE OF CORRECTION

PATENT NO. : 6,897,339 B2
DATED : May 24, 2005
INVENTOR(S) : Turchetta et al.

It is certified that error appears in the above-identified patent and that said Letters Patent is hereby corrected as shown below:

Column 1,
Line 9, replace "italian" with -- Italian --.

Column 3,
Line 55, replace "115÷120°C." with -- 115-120°C. --.

Column 4,
Line 10, replace "1.methoxy" with -- 1-methoxy --; and
Line 32, replace "1methoxy" with -- 1-methoxy --.

Signed and Sealed this

Twenty-fourth Day of January, 2006

JON W. DUDAS
*Director of the United States Patent and Trademark Office*